US008778025B2

(12) United States Patent
Ragab et al.

(10) Patent No.: US 8,778,025 B2
(45) Date of Patent: *Jul. 15, 2014

(54) ROTATABLE CAM LIFT FOR AN EXPANDABLE BONE CAGE

(76) Inventors: Ashraf A. Ragab, Largo, FL (US); James A. Rinner, Raymond, WI (US)

( * ) Notice: Subject to any disclaimer, the term of this patent is extended or adjusted under 35 U.S.C. 154(b) by 285 days.

This patent is subject to a terminal disclaimer.

(21) Appl. No.: 12/986,100

(22) Filed: Jan. 6, 2011

(65) Prior Publication Data

US 2012/0029637 A1  Feb. 2, 2012

Related U.S. Application Data

(63) Continuation-in-part of application No. 12/484,797, filed on Aug. 2, 2010, now Pat. No. 8,496,706.

(51) Int. Cl.
*A61F 2/44* (2006.01)

(52) U.S. Cl.
USPC ....................................... 623/17.11

(58) Field of Classification Search
USPC ................ 623/17.11–17.16; 606/248–249
See application file for complete search history.

(56) References Cited

U.S. PATENT DOCUMENTS

| | | | | |
|---|---|---|---|---|
| 5,554,191 A * | 9/1996 | Lahille et al. | ........... | 623/17.11 |
| 6,190,414 B1 * | 2/2001 | Young et al. | ........... | 623/17.15 |
| 6,454,807 B1 * | 9/2002 | Jackson | ........... | 623/17.15 |
| 6,500,205 B1 * | 12/2002 | Michelson | ........... | 623/17.16 |
| 6,569,201 B2 * | 5/2003 | Moumene et al. | ........... | 623/17.11 |
| 6,685,742 B1 * | 2/2004 | Jackson | ........... | 623/17.11 |
| 6,743,255 B2 * | 6/2004 | Ferree | ........... | 623/17.11 |
| 6,793,679 B2 * | 9/2004 | Michelson | ........... | 623/17.16 |
| 6,849,093 B2 * | 2/2005 | Michelson | ........... | 623/17.15 |
| 6,852,129 B2 * | 2/2005 | Gerbec et al. | ........... | 623/17.15 |
| 6,962,606 B2 * | 11/2005 | Michelson | ........... | 623/17.16 |
| 6,979,353 B2 * | 12/2005 | Bresina | ........... | 623/17.16 |
| 7,094,257 B2 * | 8/2006 | Mujwid et al. | ........... | 623/17.15 |
| 7,300,465 B2 * | 11/2007 | Paul et al. | ........... | 623/17.11 |
| 7,431,735 B2 * | 10/2008 | Liu et al. | ........... | 623/17.11 |
| 7,445,636 B2 * | 11/2008 | Michelson | ........... | 623/17.15 |
| 7,828,848 B2 * | 11/2010 | Chauvin et al. | ........... | 623/17.16 |
| 7,972,363 B2 * | 7/2011 | Moskowitz et al. | ........... | 606/246 |
| 8,100,972 B1 * | 1/2012 | Bruffey et al. | ........... | 623/17.11 |
| 2001/0034553 A1 * | 10/2001 | Michelson | ........... | 623/17.11 |
| 2002/0072801 A1 * | 6/2002 | Michelson | ........... | 623/17.11 |
| 2002/0128716 A1 * | 9/2002 | Cohen et al. | ........... | 623/17.15 |
| 2002/0138146 A1 * | 9/2002 | Jackson | ........... | 623/17.15 |
| 2002/0177897 A1 * | 11/2002 | Michelson | ........... | 623/17.11 |
| 2003/0050701 A1 * | 3/2003 | Michelson | ........... | 623/17.11 |
| 2003/0100949 A1 * | 5/2003 | Michelson | ........... | 623/17.11 |
| 2003/0208270 A9 * | 11/2003 | Michelson | ........... | 623/17.11 |

(Continued)

OTHER PUBLICATIONS

Stryker, VBoss Implant, http://www.stryker.com/en-us/products/spine/interbodyvertebralbodyreplacement/vbossimplant/index.htm.

(Continued)

*Primary Examiner* — Michelle C. Eckman
(74) *Attorney, Agent, or Firm* — Absolute Technology Law Group, LLC

(57) ABSTRACT

The present invention is a rotatable cam lift. The distal end of the rotatable cam lift has a plurality of cam lift lobes and nesting surfaces that allow an expandable bone cage to be expanded with maximum control and predictability of expansion and which hold the bone cage firmly in position when expanded. Cam lift edges prevent over-rotation of the cam lift.

20 Claims, 8 Drawing Sheets

(56) References Cited

U.S. PATENT DOCUMENTS

| | | | |
|---|---|---|---|
| 2004/0087947 A1* | 5/2004 | Lim et al. | 606/61 |
| 2004/0093084 A1* | 5/2004 | Michelson | 623/17.11 |
| 2005/0010294 A1* | 1/2005 | Michelson | 623/17.11 |
| 2005/0273173 A1* | 12/2005 | Gordon et al. | 623/17.16 |
| 2005/0278026 A1* | 12/2005 | Gordon et al. | 623/17.11 |
| 2006/0058878 A1* | 3/2006 | Michelson | 623/17.11 |
| 2006/0079962 A1* | 4/2006 | Michelson | 623/17.11 |
| 2007/0032871 A1* | 2/2007 | Michelson | 623/17.11 |
| 2007/0282448 A1* | 12/2007 | Abdou | 623/17.15 |
| 2008/0021559 A1* | 1/2008 | Thramann | 623/17.16 |
| 2008/0046090 A1* | 2/2008 | Paul et al. | 623/17.16 |
| 2009/0198339 A1* | 8/2009 | Kleiner et al. | 623/17.16 |
| 2009/0270991 A1* | 10/2009 | Michelson | 623/17.16 |
| 2010/0049324 A1* | 2/2010 | Valdevit et al. | 623/17.16 |
| 2010/0057208 A1* | 3/2010 | Dryer et al. | 623/17.16 |
| 2010/0168862 A1* | 7/2010 | Edie et al. | 623/17.16 |
| 2011/0130835 A1* | 6/2011 | Ashley et al. | 623/17.11 |

OTHER PUBLICATIONS

Globus Medical, XPand intervertebral fusion device, http://www.globusmedical.com/index.php?option=com_k2&view=item&layout=item&id=266&Itemid=318.

* cited by examiner

ROTATABLE CAM LIFT FOR AN EXPANDABLE BONE CAGE

CROSS-REFERENCE TO RELATED APPLICATIONS

This application is a continuation-in-part application that claims priority to U.S. Nonprovisional application Ser. No. 12/848,797 filed on Aug. 2, 2010, and herein incorporated by reference.

FIELD OF INVENTION

The present invention relates to the field of implants and more particularly to a rotatable cam lift for an expandable and adjustable bone cage for spinal fusions.

GLOSSARY

Figure 1:
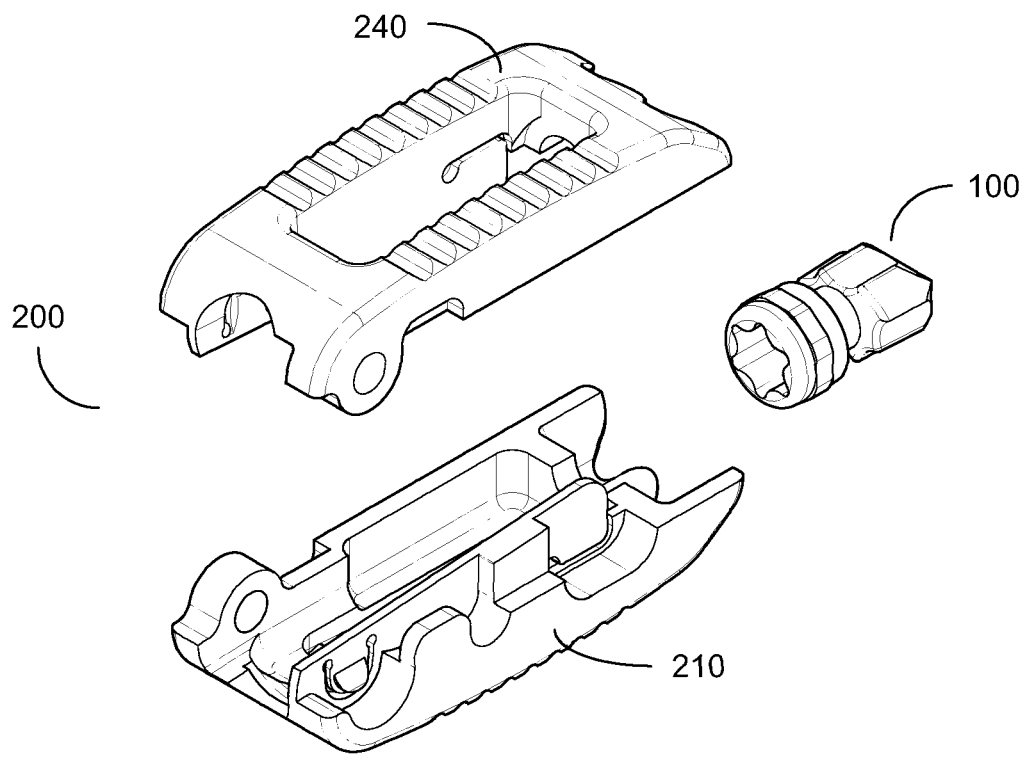
FIG. 1 illustrates an exploded view of an exemplary embodiment of a rotatable cam lift and an expandable bone cage.

As used herein, the term "bone cage" refers to an implant that is inserted into the space between vertebrae bodies replacing a damaged vertebra disc and restoring the spacing between the vertebrae.

As used herein, the term "cam lift" refers to a component with a rotational driving surface used to expand a bone cage. A cam lift may further serve a safety and control function. For example, a cam lift may be structurally designed to allow only a certain amount of expansion (e.g., 1 mm to 2 mm) to prevent over rotation.

As used herein, the term "cam lift shaft" refers to the circular portion of a cam lift that is placed between the bearing surfaces of the upper and lower bodies of a bone cage.

As used herein, the term "driver" refers to an instrument used to rotate a cam lift.

As used herein, the term "driving surface" refers to the portion of the cam lift which the driver engages.

As used herein, the term "positional flats" refers to a series of segments that encircle a portion of a cam lift and mate with the spring tab of the lower and upper body members of a bone cage.

As used herein, the term "positional lobes" refers to a series of flattened segments that encircle a portion of a cam lift. When the cam lift is rotated, the positional lobes press against the spring tab of the lower and upper body members of a bone cage.

As used herein, the term "spring tab" refers to a portion of the lower and upper body members of a bone cage that flexes during rotation of the cam lift and returns to position when the final position of the cam lift is reached.

BACKGROUND

Spinal fusion surgery for degenerative disc disease involves removing the damaged disc and replacing it with bone grafted from another site on the patient's body, bone from a donor, or artificial or synthetic bone graft material that stimulates bone growth to fuse, or join, the two vertebrae together to stabilize the spine. In all spinal interbody fusion surgeries, disc material is removed. A spacer, referred to as a "cage" is then inserted into the disc space. It is critical that the cage placed in the space formerly occupied by the disc has effective contact with the endplates of the vertebrae in order for the surgery to promote the fusion of the vertebrae and to avoid fracture of the endplates.

There are many versions of bone cages known in the art, and many attempts have been made to solve the problem of stable placement of bone cages with the optimum and controlled contact with the vertebral endplates. However, devices known in the art are associated with problems due to incomplete or uncontrolled contact between the endplates of the vertebral bodies and the upper and lower surfaces of the cage. Many attempts have been made in the art to create a bone cage which can be adjusted or positioned to account for physiological differences in patients and achieve pressure reduction.

Expandable bone cages are known in the art. An expandable bone cage may be expanded after it is inserted, allowing the surgeon to adjust the height of the bone cage to fit each specific patient. One example of an expandable bone cage is the VBoss Implant by Stryker. The VBoss Implant has an expandable column with modular end caps that are available in 5 diameters with 0, 5, or 10 degree angles to enhance restoration of lordsis. The XPand® by Globus Medical is an expandable cage that comes in a variety of footprints, heights, and lordotic angles. Both of these devices can be expanded vertically; however, these cages are indicated in cases to replace the whole vertebra body after the entire vertebral bone is removed.

U.S. Pat. No. 6,852,129 (Gerbec '129) teaches a wedge-shaped bone fusion implant with expandable sidewalls that allows the height of the implant to be adjusted when a component is inserted for expansion. This design requires that the physician manually control expansion and determine the position of the plates of the device without mechanical guidance or physical precision. In addition, the flattened and rectangular plates of the device do not accomplish effective contact with the endplates, and this leaves a gap between the surfaces of the device and the endplates.

U.S. Pat. No. 6,962,606 (Michelson '606) teaches an adjustable "push in" implant by which the "front, back or both" of the implants are raised by "the same or various amounts." The implant taught by Michelson '606 is expandable; however, placement of the Michelson '606 device requires a rectangular "blocker" component to keep the ends apart and the expansion is not effectively controlled. The lack of controlled expansion of the device may result in substantial risk to a patient because the bone cage may pack or break through the bone of the vertebral bodies if expanded too far. In addition, this device has only two positions: open and closed.

It is desirable to have a component for a bone cage which allows the bone cage to be expanded with maximum control and predictability of expansion.

It is desirable to have a reliable means for expanding a bone cage device.

SUMMARY OF THE INVENTION

The present invention is a rotatable cam lift for expanding an expandable bone cage. The rotatable cam lift is designed for use with the expandable bone cage disclosed in U.S. patent application Ser. No. 12/848,797, filed on Aug. 2, 2010, and herein incorporated by reference.

The rotatable cam lift apparatus is comprised of a cam lift shaft, an expanding component attached to the distal end of said cam lift shaft, and a driving component attached to the proximal end of said cam lift shaft. The expanding component has a plurality of cam lift lobes, cam lift edges, and nesting surfaces, which mate with a cam lift follower on the lower and upper bodies of the bone cage. The driving component has a rotational driving surface adapted to receive a driver and a plurality of positional flats and positional lobes that encircle the expanding component.

DETAILED DESCRIPTION OF INVENTION

For the purpose of promoting an understanding of the present invention, references are made in the text to exemplary embodiments of a rotatable cam lift for an expandable bone cage, only some of which are described herein. It should be understood that no limitations on the scope of the invention are intended by describing these exemplary embodiments. One of ordinary skill in the art will readily appreciate that alternate but functionally equivalent shapes, components, and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 illustrates an exploded view of an exemplary embodiment of rotatable cam lift 100 for expandable bone cage 200. In the embodiment shown, expandable bone cage 200 is comprised of lower body 210 and upper body 240, and rotatable cam lift 100 is placed between lower body 210 and upper body 240.

In the embodiment shown, rotatable cam lift 100 and bone cage 200 are comprised of titanium with a gold anodize finish; however, in other embodiments, may be comprised of another material including, but not limited to PEEK (polyether ether ketone), tricalcium phosphate, ceramic, metallic alloys, or any other implantable material and/or may have no finish or another type of finish.

Figure 2:
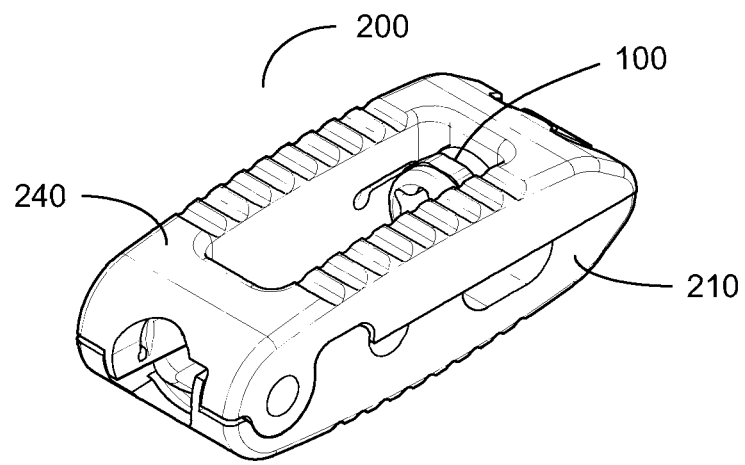
FIG. 2 illustrates a perspective view of the proximal end of an exemplary embodiment of a rotatable cam lift placed in an expandable bone cage.

FIG. 2 illustrates a perspective view of the proximal end of an exemplary embodiment of rotatable cam lift 100 placed between lower body 210 and upper body 240 of expandable bone cage 200. Rotatable cam lift 100 is accessible through the proximal end of bone cage 200 between lower body 210 and upper body 240.

Figure 3:
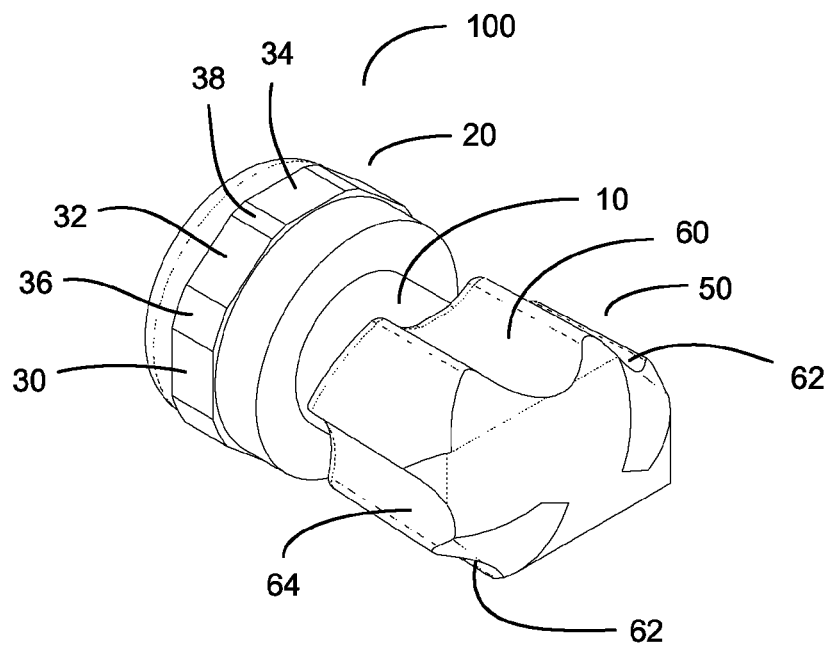
FIGS. 3 and 4 illustrate perspective views of an exemplary embodiment of a rotatable cam lift.
Figure 4:
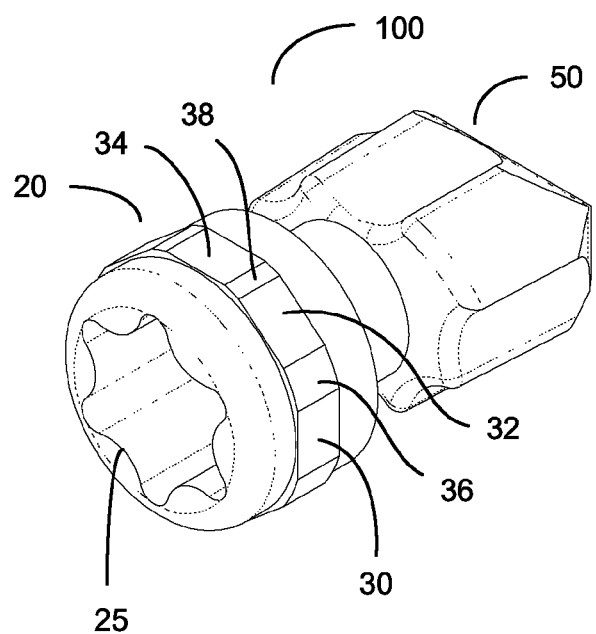

FIGS. 3 and 4 illustrate perspective views of an exemplary embodiment of rotatable cam lift 100 comprised of cam shaft 10, driving component 20, and expanding component 50. Driving component 20 is located on the proximal end of cam shaft 10 and expanding component 50 is located on the distal end of cam shaft 10.

Figure 8:
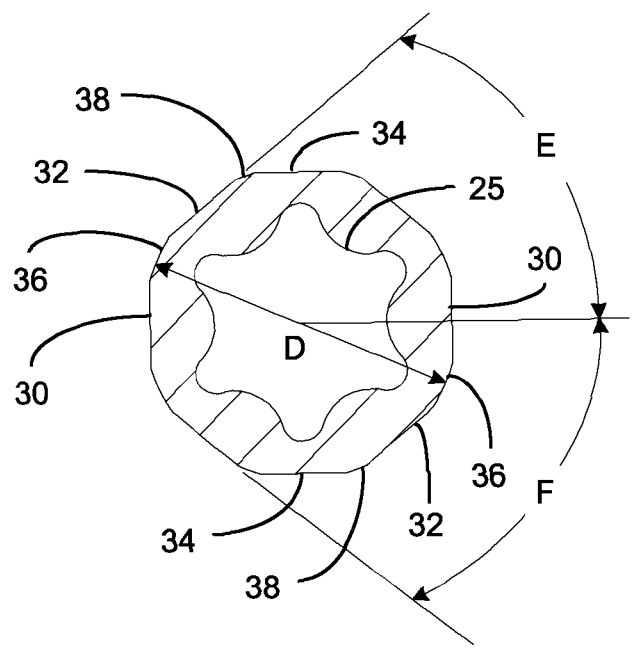
FIG. 8 illustrates a sectional view of an exemplary embodiment of a rotatable cam lift taken along line 8 of FIG. 6.

Driving component 20 includes rotational driving surface 25 (FIG. 4) on the proximal end of rotatable cam lift 100 and a plurality of positional flat pairs 30, 32, 34 and positional lobe pairs 36, 38 which encircle driving component 20 (see FIG. 8). Positional flat pairs 30, 32, 34 and positional lobe pairs 36, 38 are positioned so that the corresponding flats and lobes are diametrically opposed.

Positional flat pairs 30, 32, 34 engage a spring tab on lower body 210 (not shown) and upper body 240 (not shown) when bone cage 200 is in the closed/first, expanded second, and expanded third positions, respectively, helping to retain rotatable cam lift 100 in position and providing the surgeon with additional control when placing and expanding bone cage 200. When rotatable cam lift 100 is rotated between the closed/first position and an expanded position, positional lobe pairs 36, 38 press against the spring tabs which flex, then return to position when the final position of bone cage 200 is reached.

In the embodiment shown, rotational driving surface 25 is a female configuration with a hexalobe design with six driving slots that correspond to and are adapted to receive a hexalobe driver. In other embodiments, rotational driving surface 25 may be a male configuration, any polygon or another shape, and/or have any number or style of driving slots to correspond to a particular style of driver.

Figure 7:
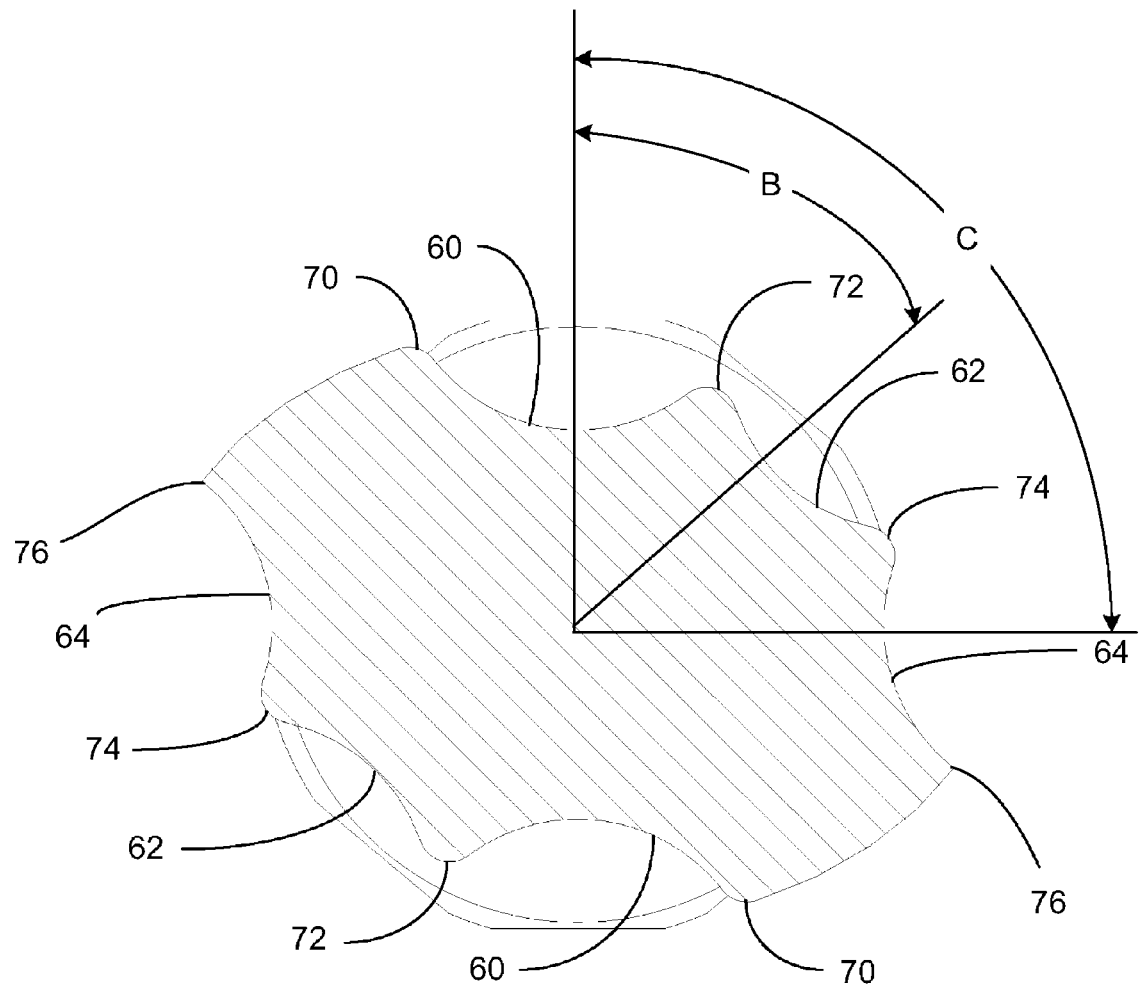
FIG. 7 illustrates a sectional view of an exemplary embodiment of a rotatable cam lift taken along line 7 of FIG. 6.

Expanding component 50 includes nesting surface pairs 60, 62, 64 (see FIGS. 7 and 10), cam lift lobe pairs 70, 72, 74, and cam lift edges 76 (see FIG. 7). When rotatable cam lift 100 is positioned between lower body 210 and upper body 240 of bone cage 200 (not shown), one of nesting surface pairs 60, 62, 64 mates with cam lift followers 215, 245 (not visible) on lower body 210 and upper body 240, respectively. When bone cage 200 is in the closed/first position, rotatable cam lift 100 is in the closed/first position and nesting surface pair 60 mates with cam lift followers 215, 245 of lower body 210 and upper body 240 (see FIG. 14).

Figure 15:
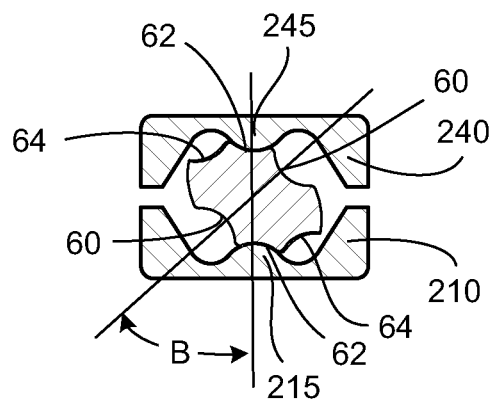
FIG. 15 illustrates a sectional view of an exemplary embodiment of a rotatable cam lift and a bone cage in the expanded second position.

To expand bone cage 200 to an expanded second position, rotatable cam lift 100 is rotated one step so that nesting surface pair 62 mates with cam lift followers 215, 245 of lower body 210 and upper body 240 (see FIG. 15). Nesting surface pairs 64 mate with cam lift followers 215, 245 when rotatable cam lift 100 is rotated to the expanded third position (see FIG. 16).

In various other embodiments, rotatable cam lift 100 may have more or fewer cam lift lobes and/or nesting surfaces.

Figure 5:
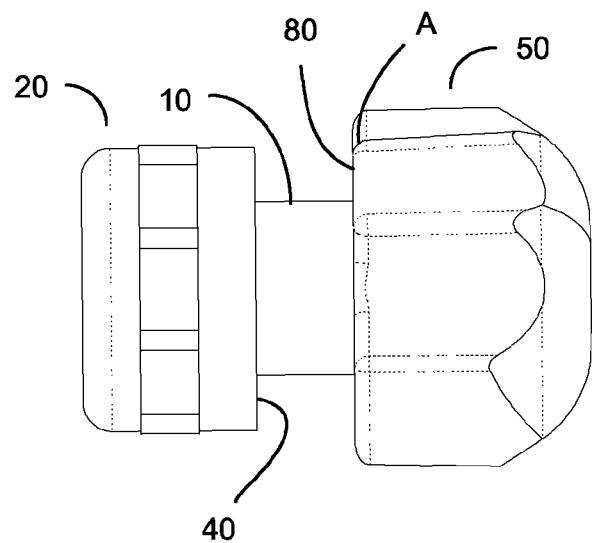
FIGS. 5 and 6 illustrate side views of an exemplary embodiment of a rotatable cam lift.
Figure 6:
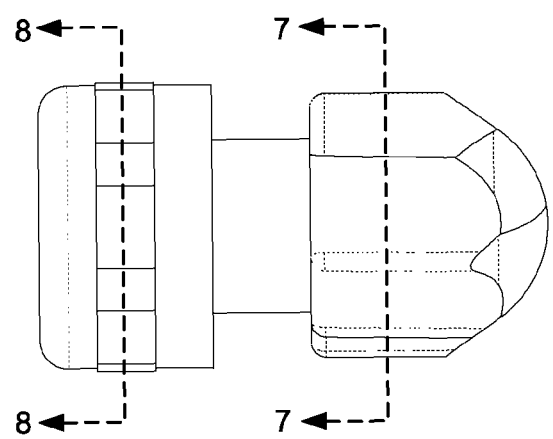

FIGS. 5 and 6 illustrate side views of an exemplary embodiment of rotatable cam lift 100. Visible in FIGS. 5 and 6 are proximal flange surface 40 and distal flange surface 80. Proximal flange surface 40 and distal flange surface 80 prevent rotatable cam lift 100 from dislocating from position in bone cage 200.

In the embodiment shown, cam shaft 10 has a length of approximately 1.7 mm and a diameter of approximately 3 mm. In various embodiments, the length and/or diameter of cam shaft 10 may vary depending on the size and design of the particular bone cage or other component in which rotatable cam lift 100 is used.

In the embodiment shown, driving component 20 has a length of approximately 3 mm and a diameter of approximately 4.9 mm, and positional flats 30, 32, 34 and positional lobes 36, 38 have a length of approximately 1 mm and are positioned approximately 1 mm from each end of driving component 20. In the embodiment shown, the outer edge of driving component 20 has a radius of approximately 0.50 mm. In various embodiments, the length of driving component 20, the diameter of driving component 20, the length of positional flats 30, 32, 34 and positional lobes 36, 38, and/or or the position of positional flats 30, 32, 34 and positional lobes 36, 38 may vary depending on the size and design of the particular bone cage or other component in which rotatable cam lift 100 is used. In addition, in various embodiments, the radius of the outer edge of driving component 20 may vary.

In the embodiment shown, expanding component 50 has a length of approximately 4.1 mm, and the backside wall of cam lift lobes has a radius of approximately 0.25 mm (designated as A). In various embodiments, the length and/or diameter of expanding component 50 may vary depending on the size and design of the particular bone cage or other component in which rotatable cam lift 100 is used. In addition, in various embodiments, the radius of the backside wall of cam lift lobes may vary.

In the embodiment shown, rotatable cam lift 100 has a length of approximately 8.8 mm; however in various embodiments rotatable cam lift 100 may be shorter or longer. For example, rotatable cam lift 100 may have a length ranging from 6 to 10 mm.

FIG. 7 illustrates a sectional view of expanding component 50 of an exemplary embodiment of rotatable cam lift 100 taken along line 7 of FIG. 6. Visible are nesting surface pairs 60, 62, 64, cam lift lobe pairs 70, 72, 74, and cam lift edges 76.

In the embodiment shown, nesting surface pair 60 is bordered by cam lift lobe pair 70 and cam lift lobe pair 72, nesting surface pair 62 is bordered by cam lift lobe pair 72 and cam lift lobe pair 74, and nesting surface pair 64 is bordered by cam lift lobe pair 74 and cam lift edge pair 76.

Figure 14:
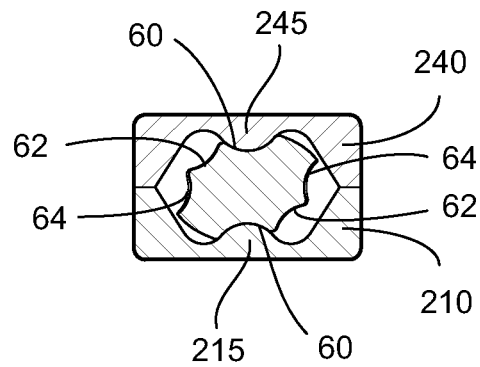
FIG. 14 illustrates a sectional view of an exemplary embodiment of a rotatable cam lift and a bone cage in the closed/first position.
Figure 16:
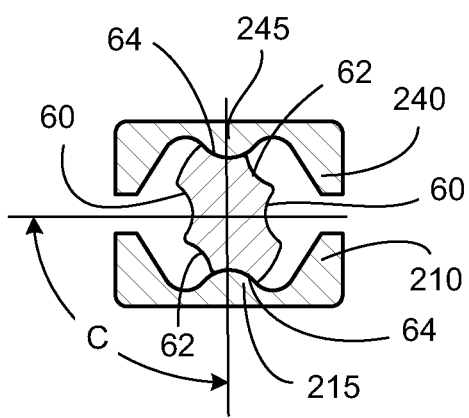
FIG. 16 illustrates a sectional view of an exemplary embodiment of a rotatable cam lift and a bone cage in the expanded third position.

In the embodiment shown, nesting surface pairs 60, 62, 64 match the angle of the surfaces of cam lift followers 215, 245 of lower body 210 and upper body 240 of bone cage 200 so that nesting surface pairs 60, 62, 64 mate with cam lift followers 215, 245 (see FIGS. 14, 15, and 16).

In the embodiment shown, the rounded shape of cam lift lobe pairs 70, 72, 74 provides for a smooth transition when rotatable cam lift 100 is rotated from a closed/first position to the expanded second position or from the expanded second position to the expanded third position.

In the embodiment shown, B represents the angle between the center of nesting surface pair 60 and the center of nesting surface pair 62, and C represents the angle between the center of nesting surface pair 60 and the center of nesting surface pair 64.

In the embodiment shown, angle B is approximately 50 degrees and angle C is approximately 90 degrees; however, in various other embodiments, angle B and/or angle C may vary depending on the size and design of the particular bone cage or other component in which rotatable cam lift 100 is used.

In the embodiment shown, the radius of the edge between the cam lift lobes of cam lift lobe pair 70 and the cam lift edges of cam lift edge pair is 76 is approximately 0.25 mm. In other embodiments, the radius may be smaller or larger depending on the shape of the cam lift lobes.

FIG. 8 illustrates a sectional view of driving component 20 of an exemplary embodiment of rotatable cam lift 100 taken along line 8 of FIG. 6. Visible are rotational driving surface 25, positional flat pairs 30, 32, 34, and positional lobe pairs 36, 38.

In the embodiment shown, the distance between the tangent lines of the positional flats in positional flat pairs 30, 32, 34 is approximately 5 mm, and the diameter (designated as D) is approximately 5.2 mm.

In the embodiment shown, angles E and F are approximately 45 degrees; however, in other embodiments, angles E and F may be smaller or larger depending on the design of driving component 20.

Figure 9:
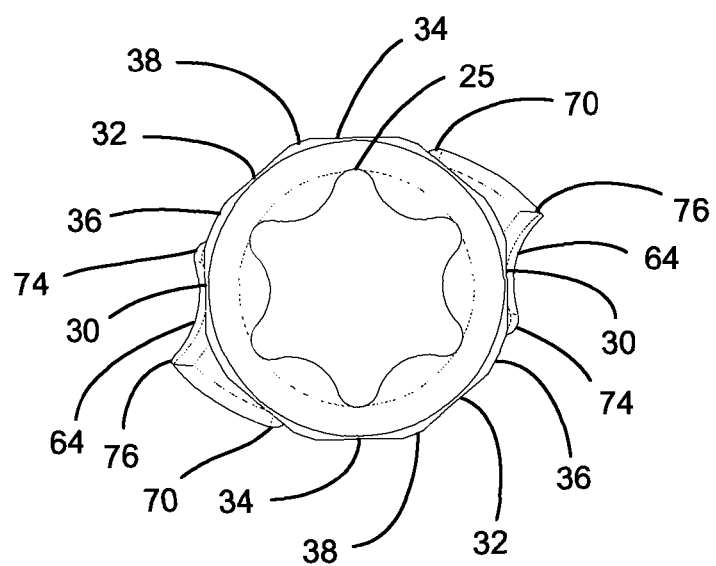
FIG. 9 illustrates an end view of the proximal end of an exemplary embodiment of a rotatable cam lift.

FIG. 9 illustrates an end view of the proximal end of an exemplary embodiment of rotatable cam lift 100. Visible are rotational driving surface 25, positional flat pairs 30, 32, 34, positional lobe pairs 36, 38, nesting surface pair 64, cam lift lobe pairs 70, 74, and cam lift edge pair 76.

Figure 10:
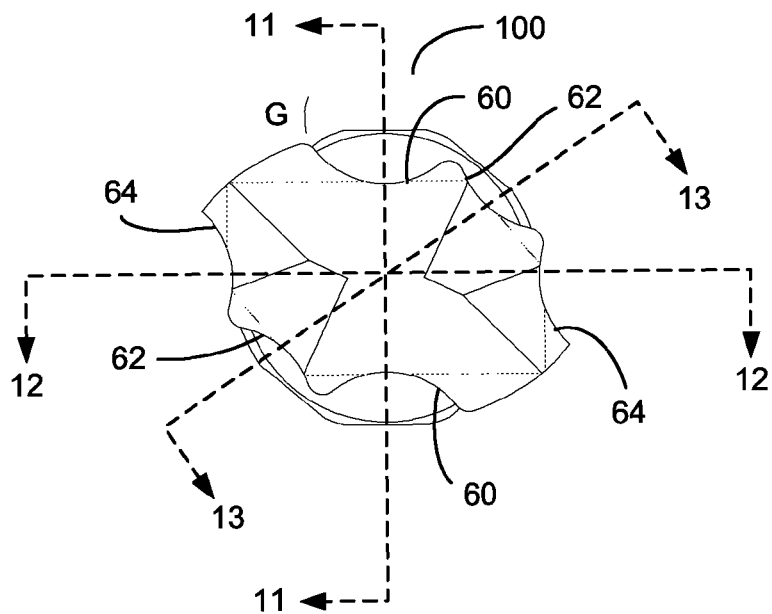
FIG. 10 illustrates an end view of the distal end of an exemplary embodiment of a rotatable cam lift.

FIG. 10 illustrates an end view of the distal end of an exemplary embodiment of rotatable cam lift 100 showing nesting surface pairs 60, 62, 64.

In the embodiment shown, the radius of the nesting surfaces 60, 62, 64 (designated as G) is approximately 1.5 mm. In other embodiments, the radius of nesting surfaces 60, 62, 64 may be smaller or larger depending on the shape of the cam lift lobes and the cam lift followers of the bone cage.

Figure 11:
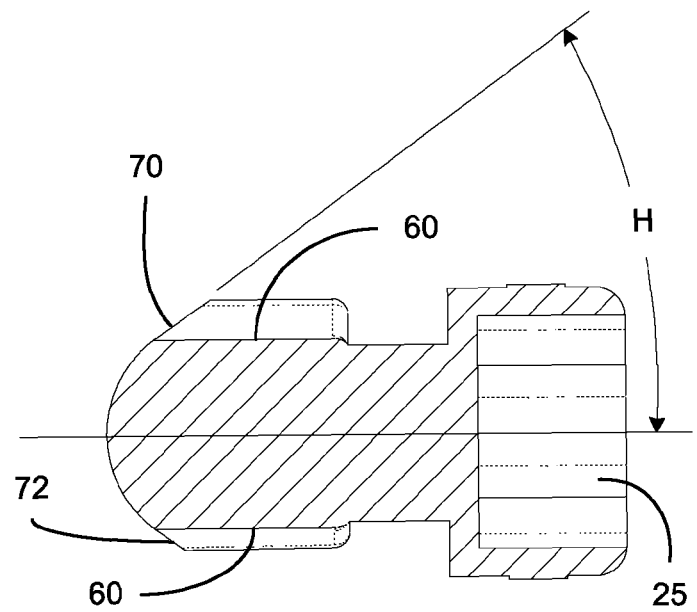
FIG. 11 illustrates a sectional view of an exemplary embodiment of a rotatable cam lift taken along line 11 of FIG. 10.

FIG. 11 illustrates a sectional view of an exemplary embodiment of rotatable cam lift 100 taken along line 11 of FIG. 10, which passes through the center of nesting surface pair 60. Also visible is one cam lift lobe of cam lift lobe pair 70 and one cam lift lobe of cam lift lobe pair 72.

In the embodiment shown, angle H represents the angle between the center line of rotatable cam lift 100 and the tangent of cam lift lobe 70 and is identical to the angle between the center line of rotatable cam lift 100 and the tangent of cam lift lobe 72. In the embodiment shown, angle H is approximately 35 degrees; however, in other embodiments may be smaller or larger depending on the shape of the cam lift lobes.

In the embodiment shown, the distance between the center line of rotatable cam lift 100 and the edge of the nesting surfaces of nesting surface pair 60 is approximately 1.6 mm and the end of expanding component 50 has a radius of approximately 2 mm.

In the embodiment shown, the depth of rotational driving surface 25 is also visible. In an exemplary embodiment, rotational driving surface 25 has a depth of approximately 2.0 to 2.5 mm depending on the size of rotatable cam lift 100 and the driver used to rotate rotatable cam lift 100.

Figure 12:
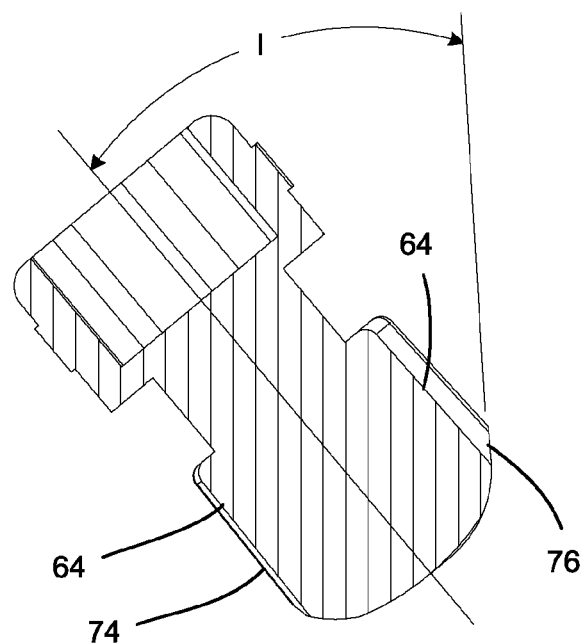
FIG. 12 illustrates a sectional view of an exemplary embodiment of a rotatable cam lift taken along line 12 of FIG. 10.

FIG. 12 illustrates a sectional view of an exemplary embodiment of rotatable cam lift 100 taken along line 12 of FIG. 10, which passes through the center of nesting surface pair 64. Also visible is one cam lift lobe of cam lift lobe pair 76 and one cam lift lobe of cam lift lobe pair 74.

In the embodiment shown, angle I represents the angle between the center line of rotatable cam lift 100 and the tangent of cam lift lobe 76 and is identical to the angle between the center line of rotatable cam lift 100 and the tangent of cam lift lobe 74. In the embodiment shown, angle I is approximately 35 degrees; however, in other embodiments may be smaller or larger depending on the shape of the cam lift lobes.

In the embodiment shown, the distance between the center line of rotatable cam lift 100 and the edge of the nesting surfaces of nesting surface pair 64 is approximately 2.6 mm and the end of expanding component 50 has a radius of approximately 2 mm.

Figure 13:
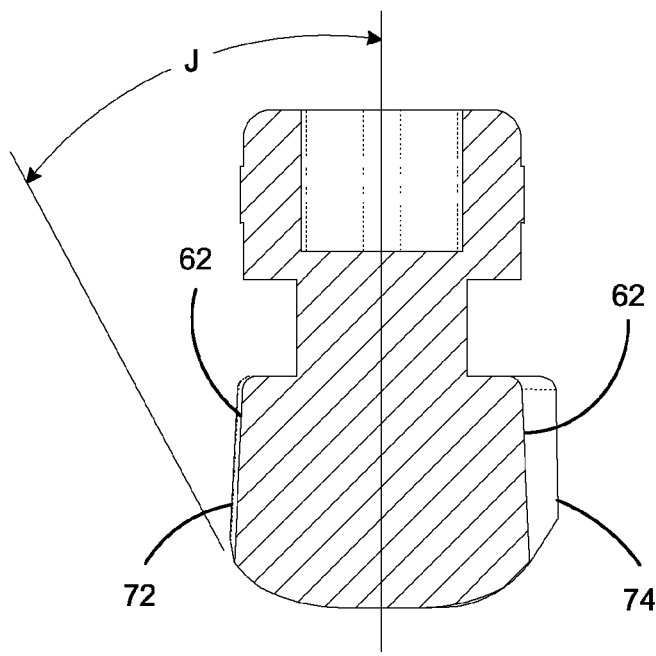
FIG. 13 illustrates a sectional view of an exemplary embodiment of a rotatable cam lift taken along line 13 of FIG. 10.

FIG. 13 illustrates a sectional view of an exemplary embodiment of rotatable cam lift 100 taken along line 13 of FIG. 10, which passes through the center of nesting surface pair 62.

In the embodiment shown, angle J represents the angle between the center line of rotatable cam lift 100 and the tangent of cam lift lobe 72 and is identical to the angle between the center line of rotatable cam lift 100 and the tangent of cam lift lobe 74. In the embodiment shown, angle J is approximately 32.4 degrees; however, in other embodiments may be smaller or larger depending on the shape of the cam lift lobes.

In the embodiment shown, the distance between the center line of rotatable cam lift 100 and the edge of the nesting surfaces of nesting surface pair 64 is approximately 1.3 mm and the end of expanding component 50 has a radius of approximately 2 mm.

FIG. 14 illustrates a sectional view of an exemplary embodiment of rotatable cam lift 100 in the closed/first position positioned between lower body 210 and upper body 240 of bone cage 200. In the embodiment shown, rotatable cam lift 100 and bone cage 200 are in the closed/first position. When rotatable cam lift 100 is in the closed/first position, nesting surface pair 60 mates with cam lift followers 215, 245 of lower body 210 and upper body 240 and lower body 210 and upper body 240 have no space between them.

FIG. 15 illustrates a sectional view of an exemplary embodiment of a rotatable cam lift 100 in the expanded second position positioned between lower body 210 and upper body 240 of bone cage 200. In the embodiment shown, rotatable cam lift 100 and bone cage 200 are in the expanded second position. To expand bone cage 200 to the expanded second position, rotatable cam lift 100 is rotated clockwise one step. When rotatable cam lift 100 is rotated, cam lift lobe pair 72 follows cam lift followers 215, 245 until nesting surface pair 62 mates with cam lift followers 215, 245, securing rotatable cam lift 100 in position. When rotatable cam lift 100 is in the expanded second position, lower body 210 and upper body 240 are spaced apart slightly.

FIG. 16 illustrates a sectional view of an exemplary embodiment of a rotatable cam lift 100 in the expanded third position positioned between lower body 210 and upper body 240 of bone cage 200. To expand bone cage 200 from the expanded second position to the expanded third position, rotatable cam lift 100 is rotated clockwise one step further so that nesting surface pair 64 mates with cam lift followers 215, 245 of lower body 210 and upper body 240. When rotatable cam lift 100 is in the expanded third position, lower body 210 and upper body 240 are spaced further apart.

When rotatable cam lift 100 is rotated clockwise from the expanded second position to the expanded third position, cam lift lobe pair 74 follows cam lift followers 215, 245 until nesting surface pair 64 mates with cam lift followers 215, 245, securing rotatable cam lift 100 into position. Cam lift edge pair 76 is higher and sharper than cam lift lobe pairs 70, 72, 74 to help prevent over-rotation of rotatable cam lift 60, which lessens risk to the patient.

In other embodiments, the cam lift lobes may be reversed so that rotatable cam lift 100 is turned counterclockwise to expand bone cage 200.

What is claimed is:

1. A bone cage apparatus comprised of:
an expandable bone cage, wherein said expandable bone cage includes:
a rounded upper body member;
a rounded lower body member;
a proximal flange surface and distal flange surface positioned to prevent said rotatable cam lift from dislocating from position in said expandable bone cage;
wherein said rounded upper body member and said lower body member are pivotally attached to each other at one end;
wherein said upper body member and said lower body member have tapered distal ends and proximal ends rounded with a constant slope;
wherein an upper cam and a lower cam have a plurality of nesting surface pairs that are in physical contact with each other when in a closed position;
wherein said rounded upper body member has a first cam shaft follower including at least one first follower surface and said lower rounded body member has a second cam shaft follower including at least one second follower surface; and
a rotatable cam lift mechanism, wherein said rotatable cam lift mechanism includes:
a cam lift shaft;
an expanding component attached to a distal end of said cam lift shaft, said expanding component having a plurality of cam lift pairs, a plurality of cam lift edges, and a plurality of nesting pairs; and
wherein each of said plurality of nesting surface pairs is bordered by one of said cam lift pair and said cam lift pair matches an angle of the surfaces of said first cam shaft follower and said second cam shaft follower of said plurality of nesting surface pairs mate with said cam lift followers;
a driving component attached to a proximal end of said cam lift shaft, said driving component having a plurality of positional flats and a plurality of positional lobes which encircle said driving component;
wherein said driving component further includes a rotational driving surface adapted to receive a driver;
wherein said cam lift shaft controls the pivotal movement of said rounded upper body member relative to said rounded lower body member from said closed position to an open position;
wherein said cam lift shaft is secured between said rounded upper body member and said rounded lower body member.

2. The apparatus of claim 1, wherein said expanding component has a first pair, a second pair, and a third pair of said cam lift pairs; a first pair, a second pair, and a third pair of said nesting pairs; and a pair of said cam lift edges.

3. The apparatus of claim 2, wherein said first pair of nesting pairs is located between said first pair of cam lift pairs and said second pair of cam lift pairs; said second pair of nesting pairs is located between said second pair of cam lift pairs and said third pair of cam lift pairs; and said third pair of nesting pairs is located between said third pair of cam lift pairs and said pair of cam lift edges.

4. The apparatus of claim 3, wherein an angle between a center of said first pair of nesting pairs and a center of said second pair of nesting pairs is 50 degrees.

5. The apparatus of claim 3, wherein an angle between the centers of said first pair of nesting pairs and the centers of said third pair of nesting pairs is 90 degrees.

6. The apparatus of claim 2, wherein said first pair, said second pair, and said third pair of nesting pairs correspond to the shape of said at least one second follower surface of said rounded lower body member and said at least one first follower surface of said rounded upper body member.

7. The apparatus of claim 6, wherein said first pair of nesting pairs mates with said first cam shaft follower and said second cam shaft follower when said bone cage is in a closed position.

8. The apparatus of claim 6, wherein said second pair of nesting pairs mates with said first cam shaft follower and said second cam shaft follower when said bone cage is in an expanded second position.

9. The apparatus of claim 6, wherein said third pair of nesting pairs mates with said first cam shaft follower and said second cam shaft follower when said bone cage is in an expanded third position.

10. The apparatus of claim 1, wherein said rotational driving surface has a plurality of driving slots.

11. The apparatus of claim 1, wherein said rotational driving surface is hexalobe-shaped with six driving slots.

12. The apparatus of claim 1, wherein said driver is rotated clockwise to expand said bone cage.

13. The apparatus of claim 1, wherein said cam lift pairs are rounded to provide a smooth transition when said cam lift shaft is rotated to expand said bone cage.

14. The apparatus of claim 1, wherein said positional flats are concave and mate with a spring tab on said lower body and said upper body of said expandable bone cage.

15. The apparatus of claim 1, wherein said positional lobes are elevated relative to said positional flat pairs to prevent accidental rotation of said cam lift shaft.

16. The apparatus of claim 14, wherein said spring tab on said lower body and said upper body flex when said positional lobes press against said spring tabs when said cam lift shaft is rotated.

17. The apparatus of claim 1, wherein said positional flats and said positional lobes are equidistance from the ends of said driving component.

18. The apparatus of claim 1, wherein said rotatable cam lift mechanism is comprised of a material selected from a group consisting of titanium, polyether ether ketone, tricalcium phosphate, ceramic, and metallic alloys.

19. The apparatus of claim 1, wherein said rotatable cam lift mechanism has a length ranging from 6 to 10 mm.

20. The apparatus of claim 19, wherein said rotatable cam lift mechanism has a length of 8.8 mm.

* * * * *